(12) United States Patent
Rowe et al.

(10) Patent No.: US 10,226,334 B2
(45) Date of Patent: Mar. 12, 2019

(54) METHOD FOR REPLACING MITRAL VALVE

(71) Applicant: Edwards Lifesciences Corporation, Irvine, CA (US)

(72) Inventors: Stanton J. Rowe, Newport Coast, CA (US); Mark Chau, Aliso Viejo, CA (US); Son V. Nguyen, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 360 days.

(21) Appl. No.: 14/584,903

(22) Filed: Dec. 29, 2014

(65) Prior Publication Data

US 2015/0127096 A1 May 7, 2015

Related U.S. Application Data

(63) Continuation of application No. 13/660,875, filed on Oct. 25, 2012, now abandoned, which is a
(Continued)

(51) Int. Cl.
*A61F 2/24* (2006.01)
*A61B 17/04* (2006.01)
(Continued)

(52) U.S. Cl.
CPC ........ *A61F 2/2418* (2013.01); *A61B 17/0401* (2013.01); *A61F 2/2427* (2013.01);
(Continued)

(58) Field of Classification Search
CPC ........ A61F 2/24; A61F 2/2418; A61F 2/2427; A61F 2/2436; A61F 2/90; A61F 2/2457;
(Continued)

(56) References Cited

U.S. PATENT DOCUMENTS

| | | | |
|---|---|---|---|
| 4,490,859 A * | 1/1985 | Black | A61F 2/2412 623/2.16 |
| 4,960,424 A | 10/1990 | Grooters | |

(Continued)

FOREIGN PATENT DOCUMENTS

| | | |
|---|---|---|
| DE | 102006052564 B3 | 12/2007 |
| DE | 102007043830 A1 | 4/2009 |

(Continued)

OTHER PUBLICATIONS

European Search Report for EP16000197, dated Jun. 29, 2016.
European Search Report for EP16002081, Completed Jan. 16, 2017.

*Primary Examiner* — Seema Mathew
(74) *Attorney, Agent, or Firm* — Klarquist Sparkman, LLP

(57) ABSTRACT

A method of implanting a prosthetic mitral valve assembly using a transapical procedure is disclosed. An incision is formed in the chest in the apex of the patient's heart. A delivery catheter containing the prosthetic mitral valve assembly is advanced over a guidewire into the patient's heart. The prosthetic mitral valve assembly is deployed from the delivery catheter into the native mitral valve. The prosthetic mitral valve assembly comprises a stent having a lower portion for placement between the leaflets of a native mitral valve and an upper portion having a flared end for placement above the annulus. The prosthetic mitral valve includes a valve portion having leaflets formed of pericardial tissue. A plurality of upwardly bent prongs are provided along an outer surface of the stent for preventing upward migration of the prosthetic mitral valve assembly after deployment.

10 Claims, 16 Drawing Sheets

Related U.S. Application Data continuation of application No. 12/113,418, filed on May 1, 2008, now abandoned.

(51) Int. Cl.
*A61F 2/90* (2013.01)
*A61L 27/36* (2006.01)
*A61L 27/50* (2006.01)
*A61B 17/00* (2006.01)

(52) U.S. Cl.
CPC .......... *A61F 2/2436* (2013.01); *A61F 2/2454* (2013.01); *A61F 2/90* (2013.01); *A61L 27/3625* (2013.01); *A61L 27/50* (2013.01); *A61B 2017/00243* (2013.01); *A61B 2017/0417* (2013.01); *A61B 2017/0496* (2013.01); *A61F 2/2457* (2013.01); *A61F 2210/0014* (2013.01); *A61F 2220/0008* (2013.01); *A61F 2220/0016* (2013.01); *A61F 2230/0054* (2013.01); *A61F 2230/0067* (2013.01); *A61F 2230/0078* (2013.01); *A61F 2250/0039* (2013.01); *A61L 2430/20* (2013.01)

(58) Field of Classification Search
CPC .... A61F 2/2442; A61F 2/2445; A61F 2/2448; A61F 2/2487; A61F 2/2412; A61F 2/246; A61F 2250/001; A61F 2210/0014; A61F 2220/0016; A61F 2/2454; A61F 2/2481; A61F 2/2451; A61F 2/2409; A61F 2/2463; A61F 2002/821; A61F 2250/0039; A61L 27/50; A61L 27/3625
See application file for complete search history.

(56) References Cited

U.S. PATENT DOCUMENTS

| | | | |
|---|---|---|---|
| 6,358,277 B1 | 3/2002 | Duran | |
| 6,458,153 B1* | 10/2002 | Bailey | A61F 2/2418 623/1.24 |
| 7,101,395 B2 | 9/2006 | Tremulis et al. | |
| 7,267,686 B2 | 9/2007 | DiMatteo et al. | |
| 7,678,145 B2 | 3/2010 | Vidlund et al. | |
| 9,078,749 B2 | 7/2015 | Lutter et al. | |
| 9,095,433 B2 | 8/2015 | Lutter et al. | |
| 9,254,192 B2 | 2/2016 | Lutter et al. | |
| 2003/0078465 A1 | 4/2003 | Pai et al. | |
| 2004/0260390 A1 | 12/2004 | Sarac et al. | |
| 2005/0075727 A1* | 4/2005 | Wheatley | A61F 2/2412 623/2.17 |
| 2005/0192581 A1* | 9/2005 | Molz | A61B 17/842 606/74 |
| 2006/0167543 A1* | 7/2006 | Bailey | A61F 2/2418 623/2.18 |
| 2006/0178700 A1* | 8/2006 | Quinn | A61B 17/00234 606/213 |
| 2006/0195183 A1* | 8/2006 | Navia | A61F 2/2409 623/2.18 |
| 2006/0241745 A1* | 10/2006 | Solem | A61F 2/2418 623/2.18 |
| 2006/0287717 A1* | 12/2006 | Rowe | A61F 2/2412 623/2.11 |
| 2007/0093890 A1 | 4/2007 | Eliasen et al. | |
| 2007/0213813 A1 | 9/2007 | Von Segesser et al. | |
| 2007/0255389 A1* | 11/2007 | Oberti | A61F 2/90 623/1.11 |
| 2007/0270943 A1 | 11/2007 | Solem et al. | |
| 2007/0282429 A1 | 12/2007 | Hauser et al. | |
| 2008/0086164 A1 | 4/2008 | Rowe | |
| 2008/0125860 A1* | 5/2008 | Webler | A61B 17/00234 623/2.36 |
| 2009/0131880 A1 | 5/2009 | Speziali et al. | |
| 2010/0280606 A1* | 11/2010 | Naor | A61F 2/2418 623/2.18 |
| 2013/0018459 A1* | 1/2013 | Maisano | A61B 17/0401 623/2.37 |
| 2014/0005778 A1* | 1/2014 | Buchbinder | A61F 2/2445 623/2.18 |
| 2014/0067048 A1* | 3/2014 | Chau | A61F 2/246 623/2.1 |
| 2014/0358223 A1* | 12/2014 | Rafiee | A61F 2/2418 623/2.13 |
| 2016/0151155 A1 | 6/2016 | Lutter et al. | |

FOREIGN PATENT DOCUMENTS

| | | |
|---|---|---|
| DE | 102007043831 A1 | 4/2009 |
| WO | 03003949 A2 | 1/2003 |
| WO | 05/087140 A1 | 9/2005 |
| WO | 2005087140 A1 | 9/2005 |
| WO | 2006127756 A2 | 11/2006 |
| WO | 2006127765 A1 | 11/2006 |
| WO | 2007140470 A2 | 12/2007 |
| WO | 2008091515 A2 | 7/2008 |
| WO | 2009033469 A1 | 3/2009 |
| WO | WO2010091653 A1 | 8/2010 |
| WO | 2010121076 A2 | 10/2010 |

* cited by examiner

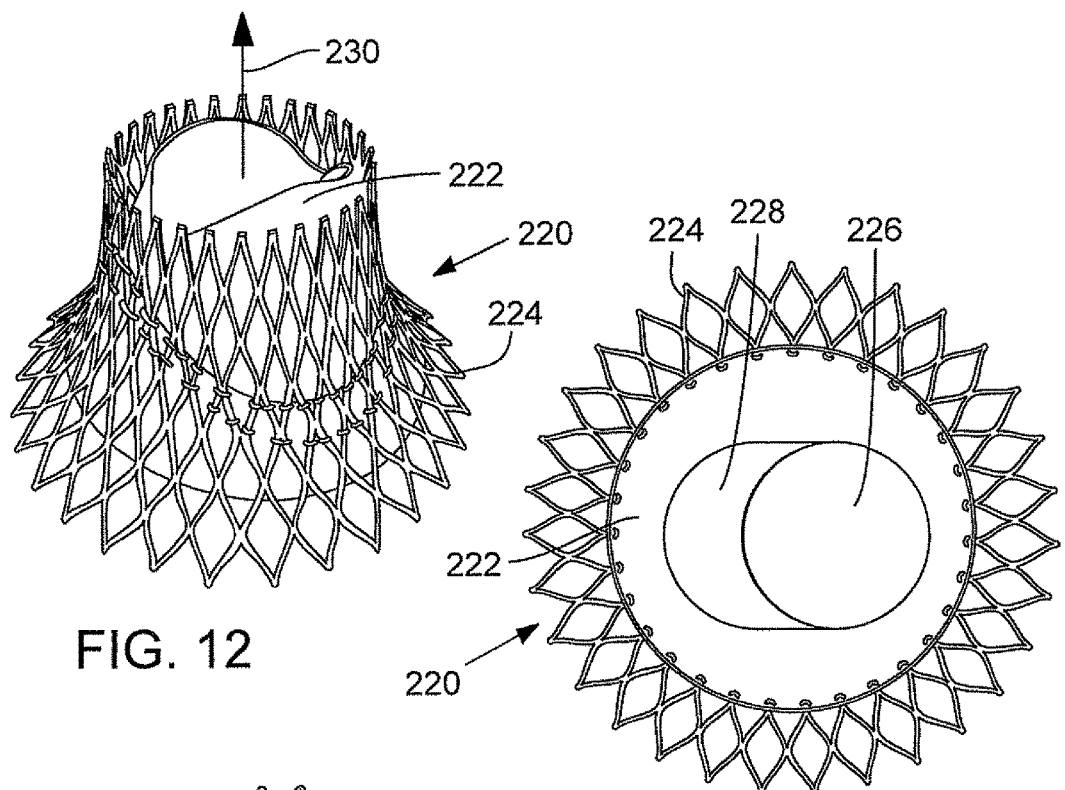
FIG. 12
FIG. 13
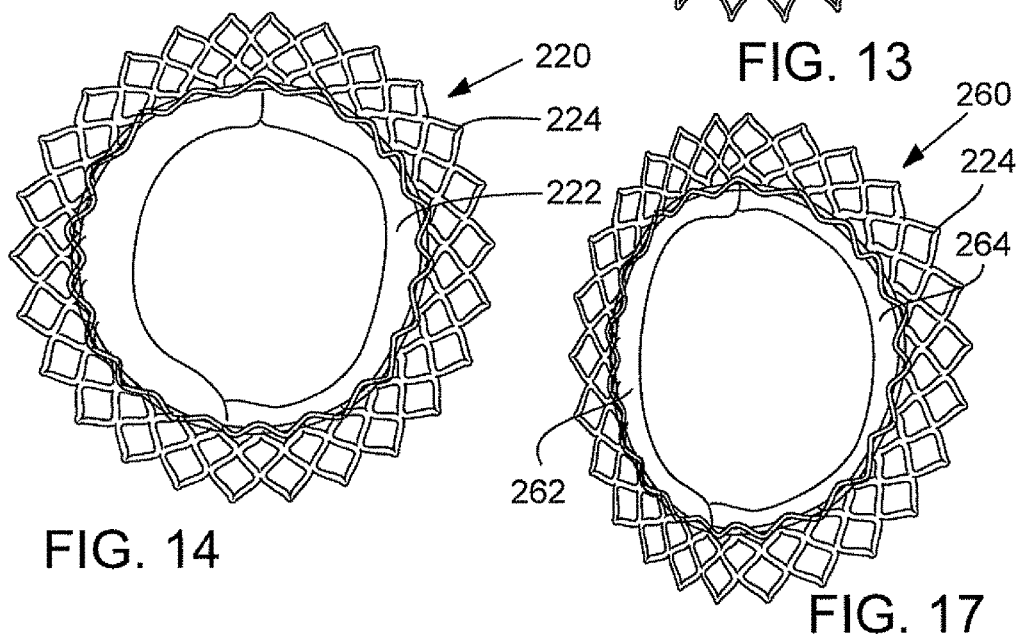
FIG. 14
FIG. 17

METHOD FOR REPLACING MITRAL VALVE

RELATED APPLICATIONS

This application is a continuation of U.S. patent application Ser. No. 13/660,875, filed Oct. 25, 2012, which is a continuation of U.S. patent application Ser. No. 12/113,418, filed May 1, 2008, the disclosure of which is incorporated by reference.

FIELD

The present disclosure concerns a prosthetic mitral heart valve and a method for implanting such a heart valve.

BACKGROUND

Prosthetic cardiac valves have been used for many years to treat cardiac valvular disorders. The native heart valves (such as the aortic, pulmonary and mitral valves) serve critical functions in assuring the forward flow of an adequate supply of blood through the cardiovascular system. These heart valves can be rendered less effective by congenital, inflammatory or infectious conditions. Such damage to the valves can result in serious cardiovascular compromise or death. For many years the definitive treatment for such disorders was the surgical repair or replacement of the valve during open heart surgery, but such surgeries are prone to many complications. More recently a transvascular technique has been developed for introducing and implanting a prosthetic heart valve using a flexible catheter in a manner that is less invasive than open heart surgery.

In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Another known technique for implanting a prosthetic aortic valve is a transapical approach where a small incision is made in the chest wall of a patient and the catheter is advanced through the apex (i.e., bottom tip) of the heart. Transapical techniques are disclosed in U.S. Patent Application Publication No. 2007/0112422, which is hereby incorporated by reference. Like the transvascular approach, the transapical approach includes a balloon catheter having a steering mechanism for delivering a balloon-expandable prosthetic heart valve through an introducer to the aortic annulus. The balloon catheter includes a deflecting segment just proximal to the distal balloon to facilitate positioning of the prosthetic heart valve in the proper orientation within the aortic annulus.

The above techniques and others have provided numerous options for high-risk patients with aortic valve stenosis to avoid the consequences of open heart surgery and cardiopulmonary bypass. While procedures for the aortic valve are well-developed, such procedures are not necessarily applicable to the mitral valve.

Mitral valve repair has increased in popularity due to its high success rates, and clinical improvements noted after repair. However, a significant percentage (i.e., about 33%) of patients still receive open-heart surgical mitral valve replacements due to calcium, stenosis, or anatomical limitations. There are a number of technologies aimed at making mitral repair a less invasive procedure. These technologies range from iterations of the Alfieri stitch procedure to coronary sinus-based modifications of mitral anatomy to subvalvular placations or ventricular remodeling devices, which would incidently correct mitral regurgitation.

However, for mitral valve replacement, few less-invasive options are available. There are approximately 60,000 mitral valve replacements (MVR) each year and it is estimated that another 60,000 patients should receive MVR, but are denied the surgical procedure due to risks associated with the patient's age or other factors. One potential option for a less invasive mitral valve replacement is disclosed in U.S. Patent Application 2007/0016286 to Herrmann. However, the stent disclosed in that application has a claw structure for attaching the prosthetic valve to the heart. Such a claw structure could have stability issues and limit consistent placement of a transcatheter mitral replacement valve.

Accordingly, further options are needed for less-invasive mitral valve replacement.

SUMMARY

A prosthetic mitral valve assembly and method of inserting the same is disclosed.

In certain disclosed embodiments, the prosthetic mitral valve assembly has a flared upper end and a tapered portion to fit the contours of the native mitral valve. The prosthetic mitral valve assembly can include a stent or outer support frame with a valve mounted therein. The assembly is adapted to expand radially outwardly and into contact with the native tissue to create a pressure fit. With the mitral valve assembly properly positioned, it will replace the function of the native valve.

In other embodiments, the mitral valve assembly can be inserted above or below an annulus of the native mitral valve. When positioned below the annulus, the mitral valve assembly is sized to press into the native tissue such that the annulus itself can restrict the assembly from moving in an upward direction towards the left atrium. The mitral valve assembly is also positioned so that the native leaflets of the mitral valve are held in the open position.

In still other embodiments, when positioned above the annulus, prongs or other attachment mechanisms on an outer surface of the stent may be used to resist upward movement of the mitral valve assembly. Alternatively (or in addition), a tether or other anchoring member can be attached to the stent at one end and secured to a portion of the heart at another end in order to prevent movement of the mitral valve assembly after implantation. A tether may also be used to decrease the stress on the leaflets of the replacement valve and/or to re-shape the left ventricle.

In still other embodiments, the prosthetic mitral valve assembly can be inserted using a transapical procedure wherein an incision is made in the chest of a patient and in the apex of the heart. The mitral valve assembly is mounted in a compressed state on the distal end of a delivery catheter, which is inserted through the apex and into the heart. Once inside the heart, the valve assembly can be expanded to its functional size and positioned at the desired location within the native valve. In certain embodiments, the valve assembly can be self-expanding so that it can expand to its functional size inside the heart when advanced from the distal end of a delivery sheath. In other embodiments, the valve assembly can be mounted in a compressed state on a balloon of the delivery catheter and is expandable by inflation of the balloon.

These features and others of the described embodiments will be more readily apparent from the following detailed description, which proceeds with reference to the accompanying drawings.

BRIEF DESCRIPTION OF THE DRAWINGS

FIG. 12 is a perspective view of a prosthetic valve assembly having a bicuspid valve, according to another embodiment.

FIG. 13 is a top view of the prosthetic valve assembly of FIG. 12 with the bicuspid valve in a closed or at-rest position.

FIG. 14 is a top view of the prosthetic valve assembly of FIG. 12 with the bicuspid valve in an open position.

FIG. 17 is a cross-sectional view of a prosthetic valve assembly having a non-uniform cross-sectional shape.

DETAILED DESCRIPTION

As used herein, the singular forms "a," "an," and "the" refer to one or more than one, unless the context clearly dictates otherwise.

As used herein, the term "includes" means "comprises." For example, a device that includes or comprises A and B contains A and B but can optionally contain C or other components other than A and B. A device that includes or comprises A or B may contain A or B or A and B, and optionally one or more other components such as C.

Figure 1:
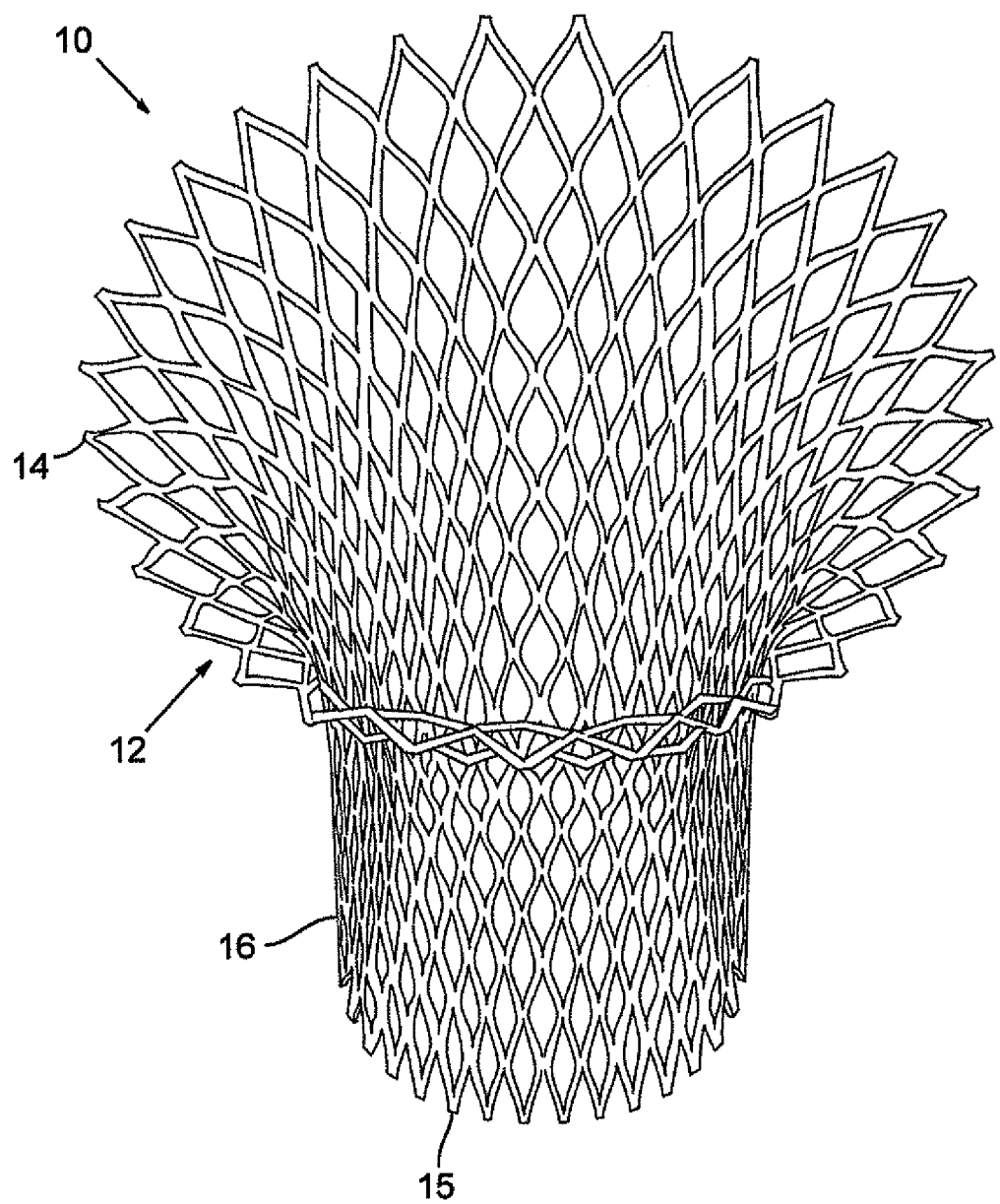
FIG. 1 is a perspective view of a stent used in certain embodiments of a mitral valve assembly.

FIG. 1 is a perspective view of a stent 10 configured for placement in a native mitral valve. The stent in this embodiment includes an upper portion 12 having an enlarged or flared end 14 that tapers to a lower portion 16 having a reduced diameter. The stent generally has a bell shape or a truncated conical shape, but other shapes can be used. The stent 10 can have a continuous taper from the flared end 14 to the lower end 15. As described below, at least the upper portion desirably tapers in a direction from the upper end to the lower end 15 so as to generally conform to the contours of the native leaflets to assist in securing the stent within the native valve. In some embodiments, the portion of the stent extending below the native leaflets can have a generally cylindrical shape or could further taper. Additionally, the length of the stent 10 can vary. In some embodiments the stent can be between 15-50 mm in length. For example, specific testing has been performed on stents having lengths of 24 mm and 46 mm in length. A circumference of the stent 10 varies along a length thereof, but is generally sized for receiving a bicuspid or tricuspid valve. An example circumference of the stent at a point in the upper portion is 30 mm, but other sizes can be used depending on the desired valve. The stent can be a self-expanding stent formed from a shape memory material, such as, for example, Nitinol. In the illustrated embodiment, the stent is formed from multiple somewhat arcuate-shaped fibers extending along the length of the stent with approximately half of the fibers bent in a first direction and half of the fibers bent in a second direction to create a criss-cross pattern. As explained further below, the stent can be delivered in a radially-compressed state using an introducer, such that after reaching the treatment site, it is advanced out of the distal end of the introducer and expands to its functional size in a relaxed state in contact with the surrounding tissue. A specific example of such a technique is shown and described below in relation to FIGS. 8A-8D.

In other embodiments, the stent 10 can be a balloon-expandable stent. In such a case, the stent can be formed from stainless steel or any other suitable materials. The balloon-expandable stent can be configured to be crimped to a reduced diameter and placed over a deflated balloon on the distal end portion of an elongate balloon catheter, as is well-understood in the art.

The flared end 14 of the stent 10 helps to secure the stent above or below the annulus of the native mitral valve (depending on the procedure used), while the tapered portion is shaped for being held in place by the native leaflets of the mitral valve.

Figure 2A:
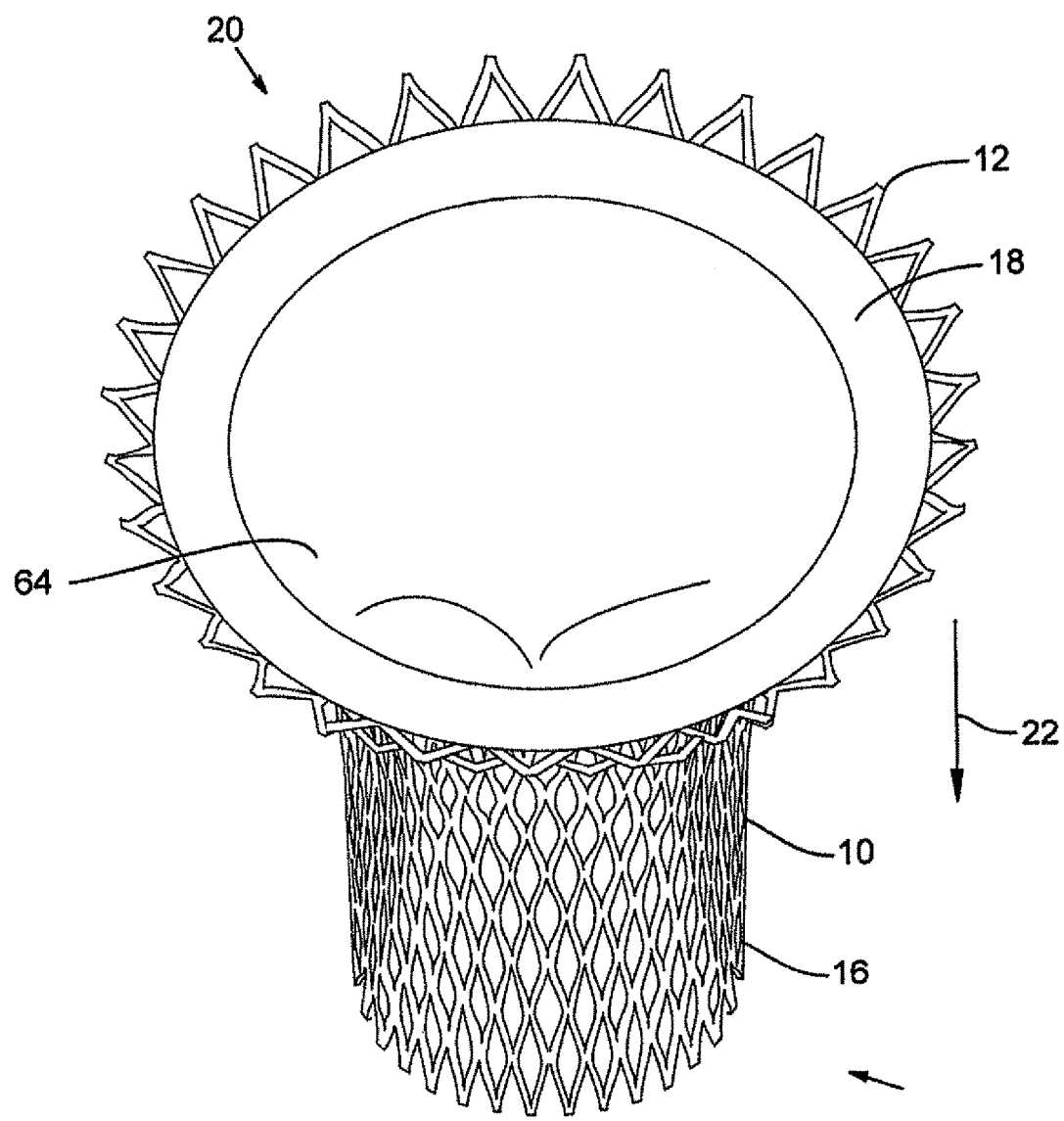
FIGS. 2A and 2B are a perspective views an embodiment of a mitral valve assembly using the stent of FIG. 1, as viewed from the top and bottom, respectively, of the assembly.
Figure 2B:
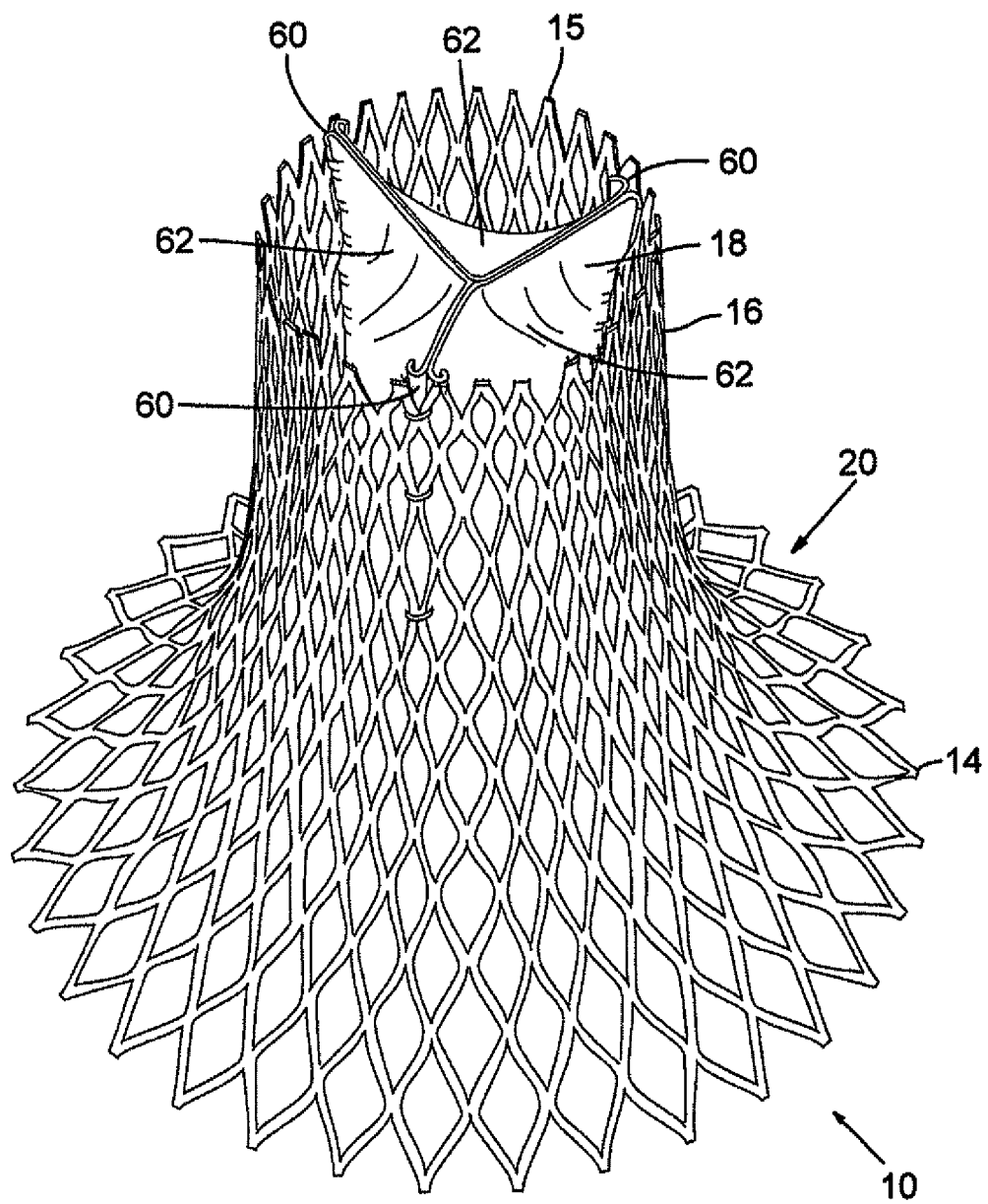

FIGS. 2A and 2B are perspective views of the stent 10 with a valve 18 inserted therein to form a mitral valve assembly 20. The valve 18 can have a leafed-valve configuration, such as a bicuspid valve configuration or the tricuspid valve configuration shown in the illustrated embodiment. As shown in FIG. 2B, the valve 18 can be formed from three pieces of flexible, pliant material connected to each other at seams 60 (also referred to as commissure tabs) to form collapsible leaflets 62 and a base, or upper end, portion 64. The valve 18 can be connected to the stent 10 at the seams 60 using, for example, sutures or other suitable connection techniques well-known in the art. Alternatively, the valve 18 can be a mechanical type valve, rather than a leafed type valve.

The valve 18 can be made from biological matter, such as natural tissue, pericardial tissue (e.g., bovine, porcine or equine pericadium), a harvested natural valve, or other biological tissue. Alternatively, the valve can be made from biocompatible synthetic materials (e.g., biocompatible polymers), which are well known in the art. The valve can be shaped to fit the contours of the stent so as to have a flared upper end portion having an upper circumference larger than a lower circumference at the lower end of the valve. Blood flow through the valve proceeds in a direction from the upper portion 12 to the lower portion 16, as indicated by arrow 22 (FIG. 2A).

Figure 3:
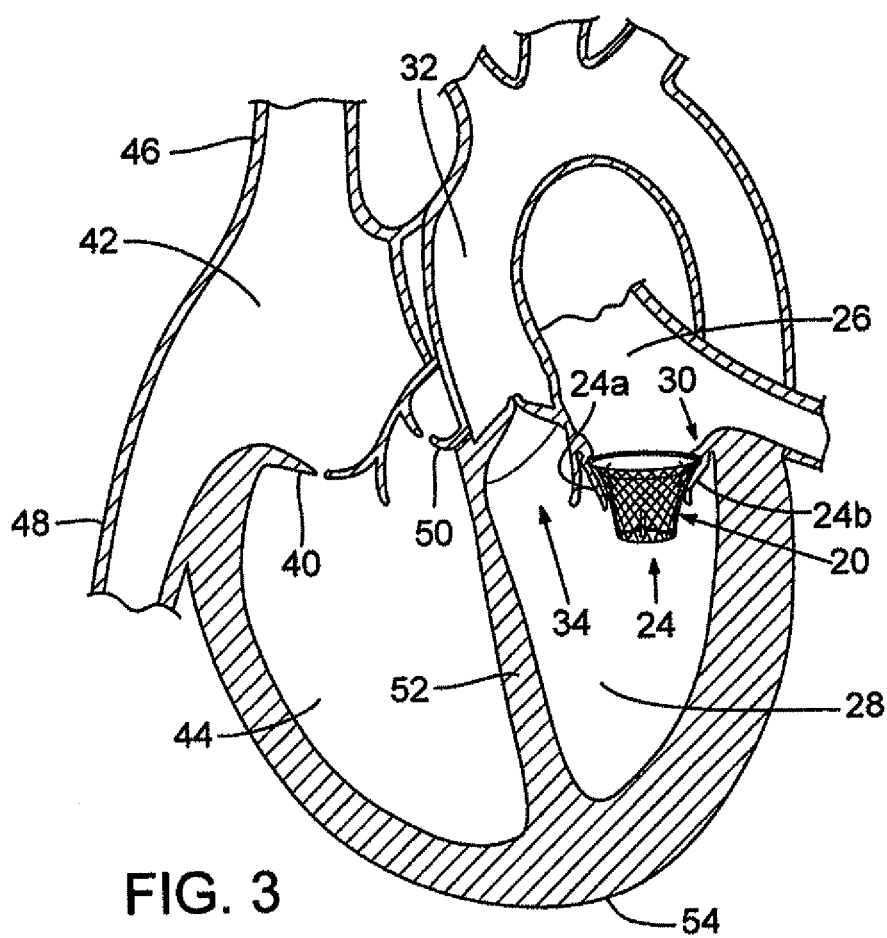
FIG. 3 is a cross-sectional view of a heart with the mitral valve assembly of FIG. 2 implanted within the native mitral valve.

FIG. 3 shows a cross-sectional view of a heart with the prosthetic mitral-valve assembly inserted into the native mitral valve. For purposes of background, the four-chambered heart is explained further. On the left side of the heart, the native mitral valve 24 is located between the left atrium 26 and left ventricle 28. The mitral valve generally comprises two leaflets, an anterior leaflet 24a and a posterior leaflet 24b. The mitral valve leaflets are attached to a mitral valve annulus 30, which is defined as the portion of tissue surrounding the mitral valve orifice. The left atrium 26 receives oxygenated blood from the pulmonary veins. The oxygenated blood that is collected in the left atrium 26 enters the left ventricle 28 through the mitral valve 24.

Contraction of the left ventricle 28 forces blood through the left ventricular outflow tract and into the aorta 32. The aortic valve 34 is located between the left ventricle 28 and the aorta 32 for ensuring that blood flows in only one direction (i.e., from the left ventricle to the aorta). As used herein, the left ventricular outflow tract (LVOT) is intended to generally include the portion of the heart through which blood is channeled from the left ventricle to the aorta.

On the right side of the heart, the tricuspid valve 40 is located between the right atrium 42 and the right ventricle 44. The right atrium 42 receives blood from the superior vena cava 46 and the inferior vena cava 48. The superior vena cava 46 returns de-oxygenated blood from the upper part of the body and the inferior vena cava 48 returns de-oxygenated blood from the lower part of the body. The right atrium 42 also receives blood from the heart muscle itself via the coronary sinus. The blood in the right atrium 42 enters into the right ventricle 44 through the tricuspid valve 40. Contraction of the right ventricle forces blood through the right ventricle outflow tract and into the pulmonary arteries. The pulmonic valve 50 is located between the right ventricle 44 and the pulmonary trunk for ensuring that blood flows in only one direction from the right ventricle to the pulmonary trunk.

The left and right sides of the heart are separated by a wall generally referred to as the septum 52. The portion of the septum that separates the two upper chambers (the right and left atria) of the heart is termed the artial (or interatrial) septum while the portion of the septum that lies between the two lower chambers (the right and left ventricles) of the heart is called the ventricular (or interventricular) septum. A healthy heart has a generally conical shape that tapers from a base to an apex 54.

As shown in FIG. 3, the mitral valve assembly 20 is positioned such that the flared end 14 of the upper portion 12 is adjacent the annulus 30 of the native mitral valve 24, while the leaflets of the native valve bear against and hold the tapered upper end portion 12 of the mitral valve assembly. The prosthetic mitral valve assembly of FIG. 3 is preferably positioned with the flared end 14 above or just below an annulus 30 of the native mitral valve. The valve assembly is configured to form a "pressure fit" with the surrounding native valve tissue; that is, the outward radial pressure of the stent bears against the surrounding tissue to assist in retaining the valve assembly in place.

Figure 4:
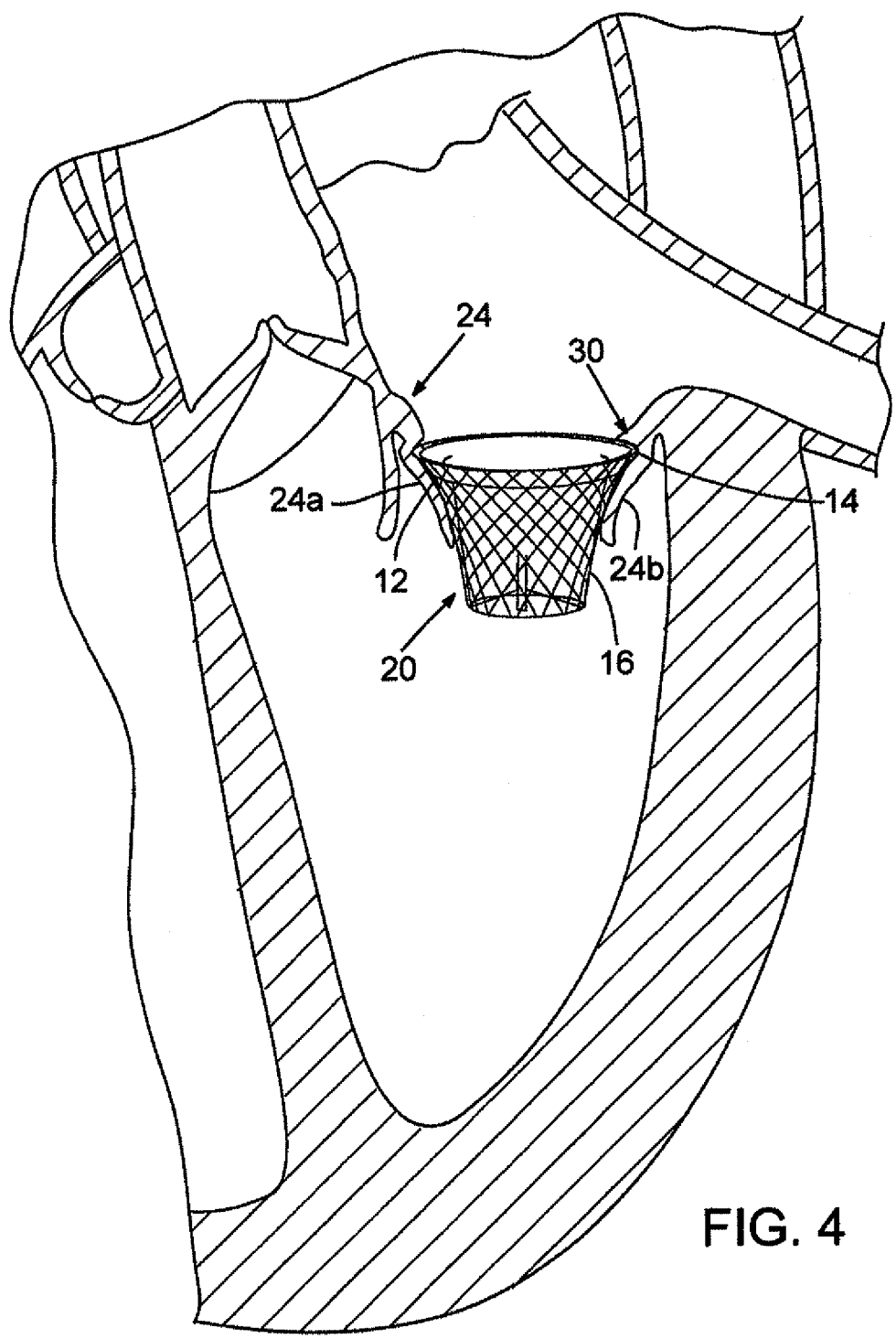
FIG. 4 is an enlarged cross-sectional view of a heart with an embodiment of the mitral valve assembly implanted below an annulus of the native mitral valve.

FIG. 4 is enlarged view of the mitral valve assembly 20 positioned below the annulus 30 of the native mitral valve 24. In particular, the flared end 14 of the stent is tucked under the annulus 30 of the native mitral valve (under the insertion point of the mitral leaflets to the left atrium), but on top of the mitral valve leaflets 24a, 24b. When deployed in this position, the mitral valve assembly exerts sufficient radial pressure outwardly to press into the native tissue, as the shape-memory material exerts an outward radial force to return the assembly to its expanded shape. As a result of the positioning of the flared end 14, the annulus 30 protrudes slightly inwardly past the flared end of the stent and acts as an annular mechanical stop preventing upward movement of the mitral valve assembly 20. The amount of outward radial pressure exerted by the mitral valve assembly 20 depends partly on the size of the stent and the type of shape-memory material used. The stent size can depend on the particular patient and the desired amount of pressure needed to hold the prosthetic mitral valve in place. The tapered upper portion 12 of the mitral valve assembly 20 desirably is shaped to fit the contours of the native mitral valve leaflets 24a, 24b, which bear against the outer surface of the stent and prevent downward motion of the assembly. Thus, due to the unique shape of the mitral valve assembly 20, it can be held in place solely by the pressure exerted by the stent radially outwardly against the surrounding tissue without the use of hooks, prongs, clamps or other grasping device.

When properly positioned, the valve assembly avoids or at least minimizes paravalvular leakage. In tests performed on a porcine heart, approximately two pounds of force or greater were applied to stents in the left atrial direction with little or no dislodgement, movement or disorientation.

Figure 5:
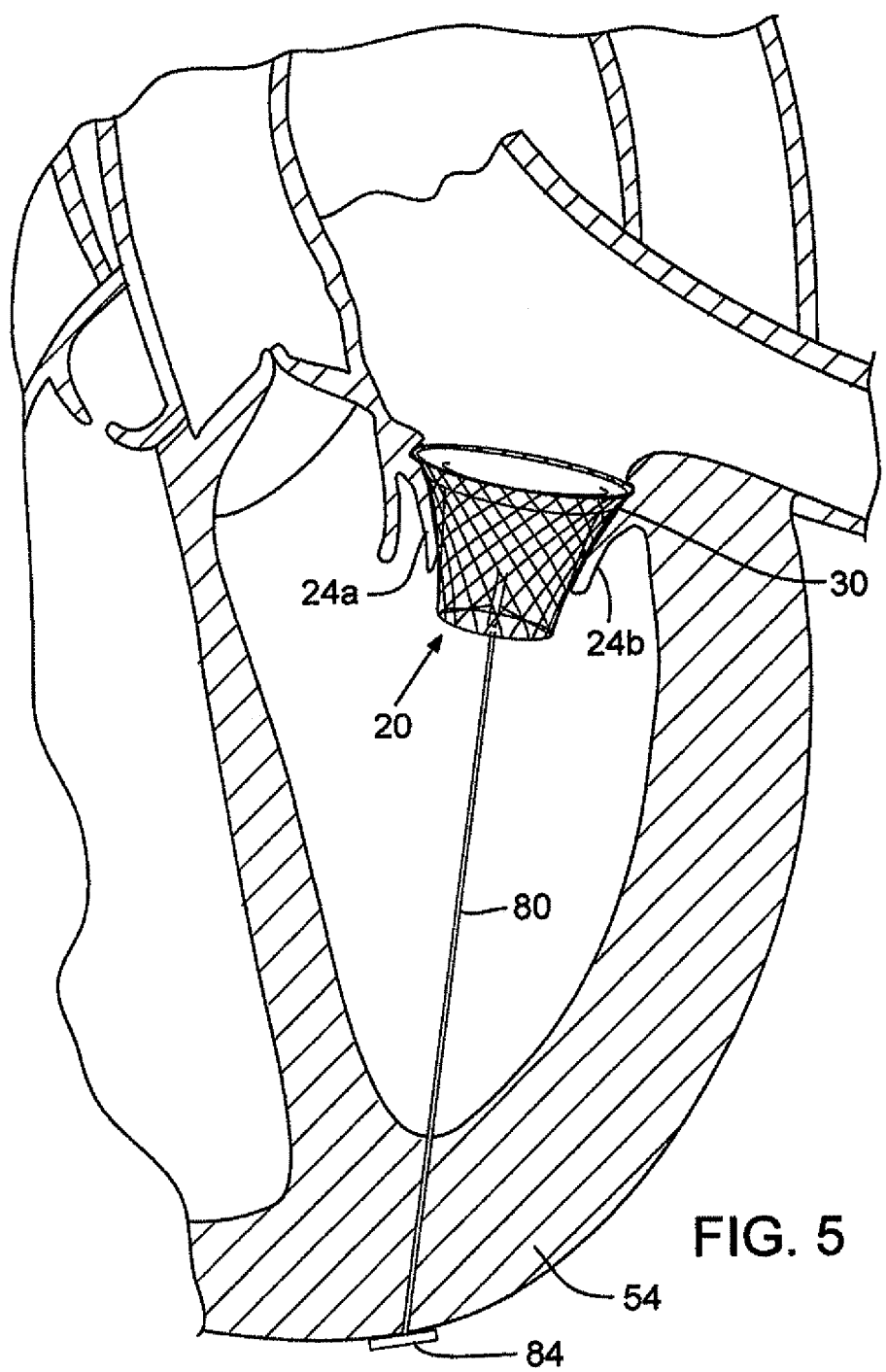
FIG. 5 is an enlarged cross-sectional view of a heart with an embodiment of the mitral valve assembly implanted within the native mitral valve wherein a tether is attached to the stent for preventing migration of the mitral valve assembly.

FIG. 5 shows an alternative positioning of the mitral valve assembly. In this position, the mitral valve assembly 20 can be secured above the native mitral valve annulus 30. The mitral valve leaflets 24a, 24b still prevent downward movement of the mitral valve assembly. However, to assist in preventing upward movement, the mitral valve assembly 20 can be anchored using a tether 80 coupled between a lower portion of the mitral valve assembly (such as by being tied to the stent) and a portion of the heart (e.g., an opposing wall). In the particular embodiment shown, the tether 80 extends through the apex 54 of the heart and is secured in place by an enlarged head portion 84 connected to the lower end of the tether outside of the apex. The tether and/or head portion can be formed of a bioresorbable material so that it eventually dissolves after the stent has grown into the wall of the native mitral valve.

Figure 6:
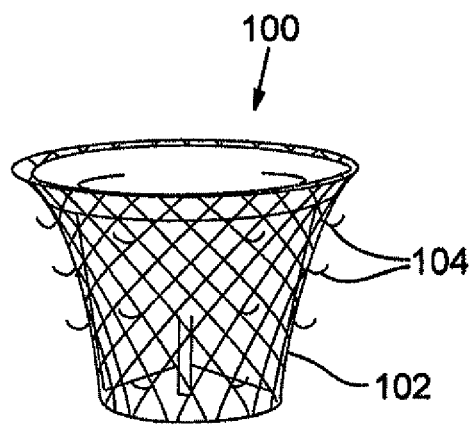
FIG. 6 is a perspective view of a mitral valve assembly having external anchoring members to assist in securing the mitral valve assembly to the surrounding tissue.

FIG. 6 shows another embodiment of a mitral valve assembly 100 that may be used with supra-annular positioning. In particular, an outer surface of a stent 102 includes anchoring members, such as, for example, prongs 104 in the form of upwardly bent hooks, that can penetrate the surrounding tissue to prevent upward migration of the assembly 100 when in place. The anchoring members may be made from the same material as the stent, but alternative materials may also be used.

Figure 7:
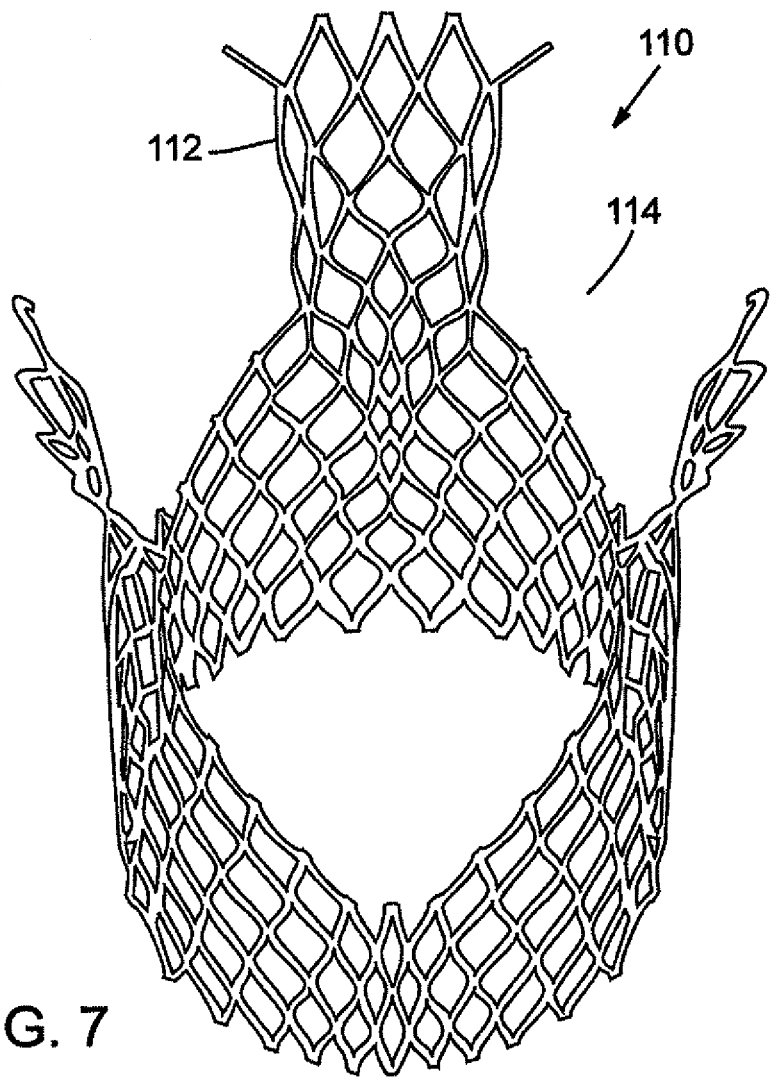
FIG. 7 is a perspective view of an embodiment of a stent having a scalloped end portion.

FIG. 7 shows another embodiment of a stent 110 that can be used. In this embodiment, an upper portion 112 of the stent is scalloped (i.e., the upper edge has one or more indented or cut-out portions 114). In some patients, the pressure exerted by the upper rim of the stent on the anterior mitral leaflet can displace the mitral curtain and anterior leaflet toward the left ventricular outflow track. The stent can be deployed such that the anterior leaflet is generally positioned within a cutout (scalloped) portion of the stent. In this manner, the scalloped stent 110 reduces the pressure on the leaflet to ensure there is no alteration of blood flow in the left ventricle.

FIGS. 8A-8D depict an embodiment of a transapical procedure for inserting the prosthetic mitral valve assembly into the native mitral valve. The replacement procedure is typically accomplished by implanting the prosthetic mitral valve assembly directly over the native leaflets, which are typically calcified. In this manner, the native leaflets 24a, 24b can assist in securing the mitral valve assembly in place.

First, an incision is made in the chest of a patient and in the apex 54 of the patient's heart. A guide wire 120 is inserted through the apex 54 and into the left ventricle. The guide wire 120 is then directed up through the mitral valve 24 and into the left atrium 26. An introducer 122 is advanced over the guide wire into the left atrium (see FIGS. 8A and 8B). A delivery catheter 124 is inserted through the introducer (see FIG. 8B). A prosthetic valve assembly 20 is retained in a crimped state on the distal end portion of the delivery catheter as the valve assembly and delivery catheter are advanced through the introducer. In one variation, the introducer 122 is formed with a tapered distal end portion 123 to assist in navigating through the chordae tendinae. The delivery catheter 124 likewise can have a tapered distal end portion 126.

Figure 8A:
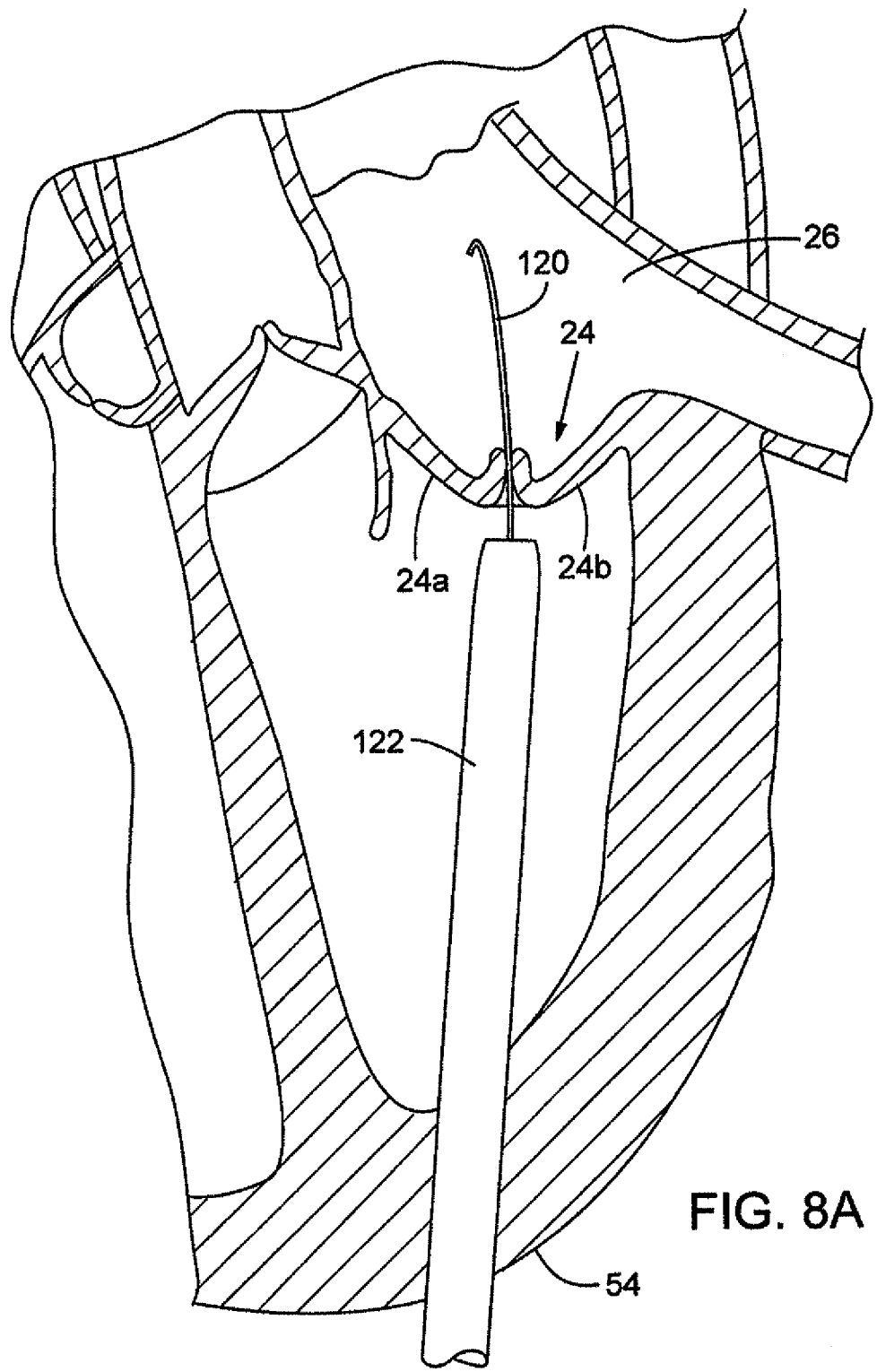
FIGS. 8A-8D are cross-sectional views showing an embodiment of the mitral valve assembly inserted using a transapical procedure.
Figure 8B:
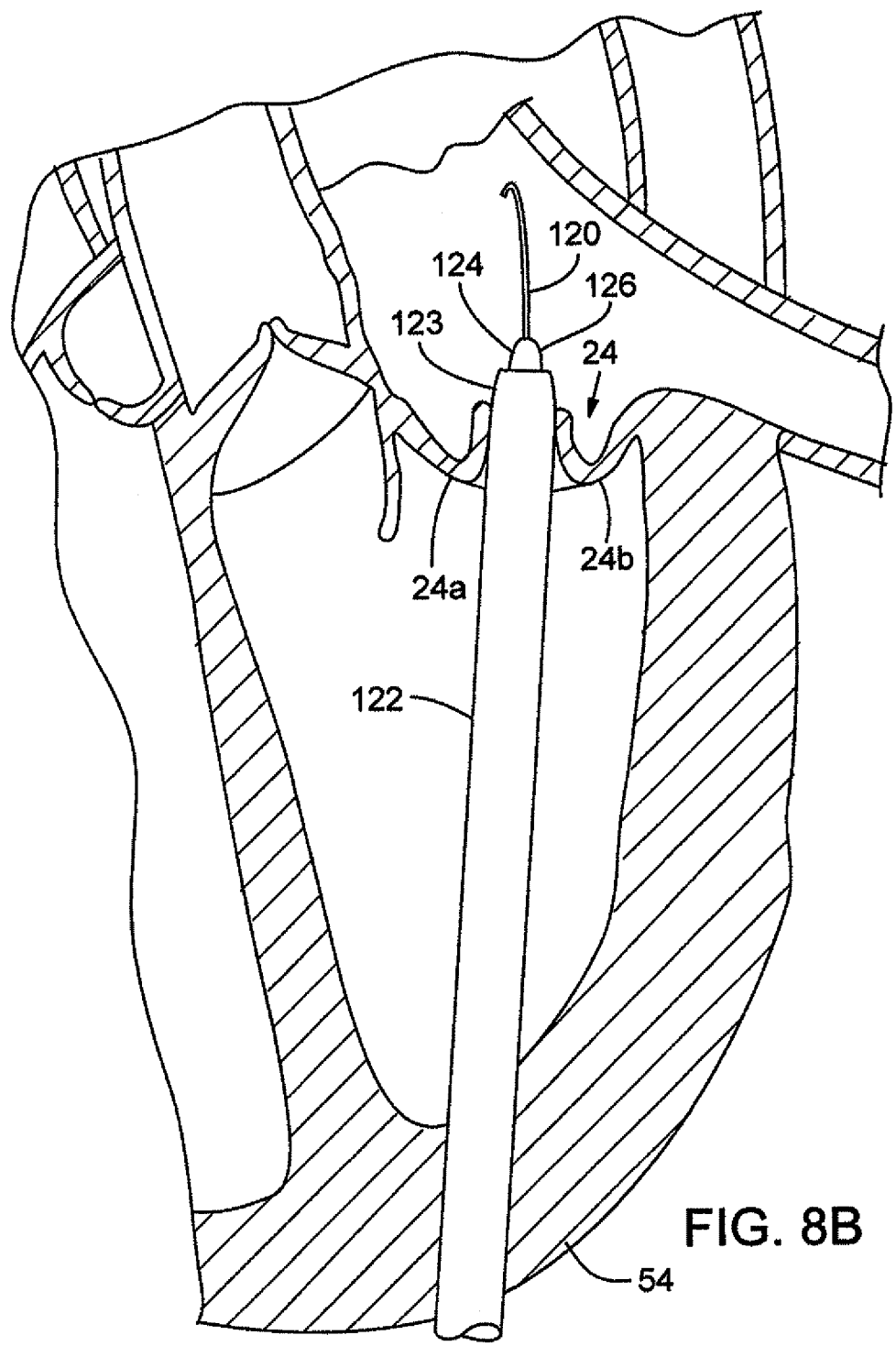
Figure 8C:
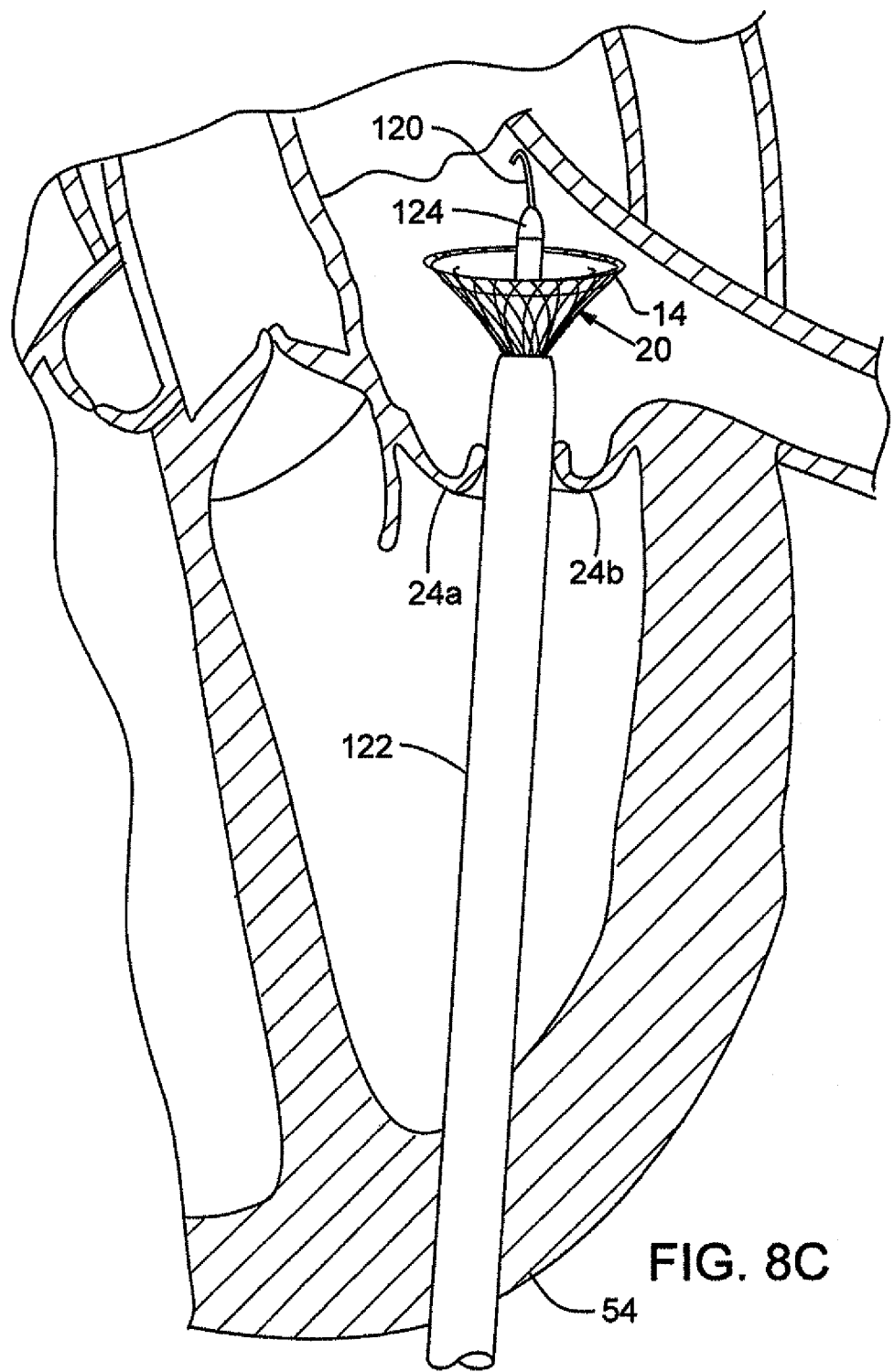
Figure 8D:
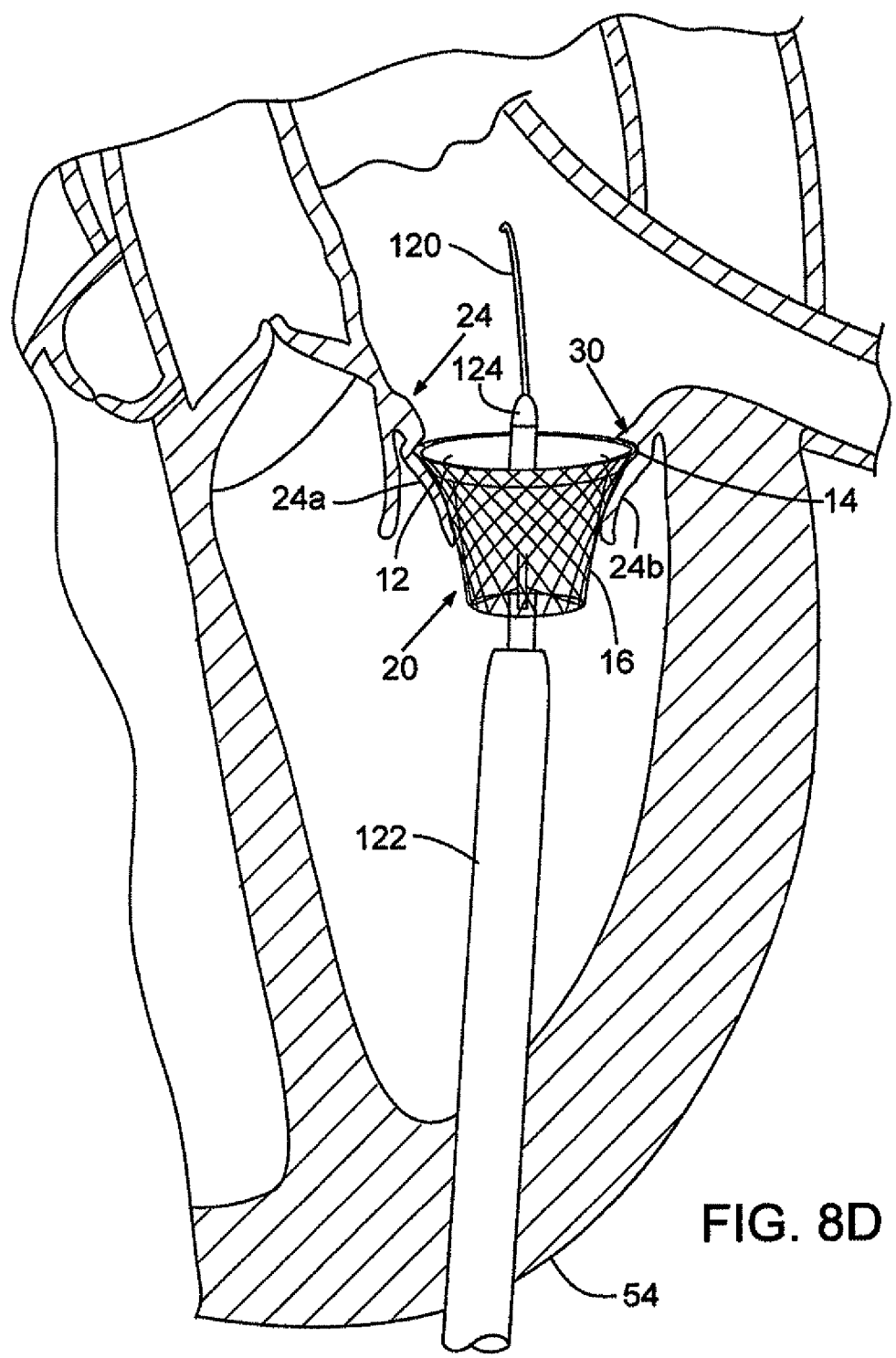

In FIG. 8C, the introducer 122 is retracted relative to the mitral valve assembly 20 for deploying the mitral valve assembly from the distal end of the introducer. To pull the valve assembly 20 into position at the intended implantation site, the valve assembly desirably is partially advanced out of the introducer to expose the flared upper end portion 12, while the remainder of the valve assembly remains compressed within the introducer (as shown in FIG. 8C). As shown, the flared end portion expands when advanced from the distal end of the introducer. The delivery catheter 124 and the introducer 122 can then be retracted together to pull the flared end into the desired position (e.g., just below the annulus of the native valve). Thereafter, the introducer can be further retracted relative to the delivery catheter to advance the remaining portion of the valve assembly 20 from the introducer, thereby allowing the entire assembly to expand to its functional size, as shown in FIG. 8D. The introducer and catheter can then be withdrawn from the patient.

Alternatively, the mitral valve assembly can be fully expanded directly in place at the implantation site by first aligning the valve assembly at the implantation site and then retracting the introducer relative to the delivery catheter to allow the entire valve assembly to expand to its functional size. In this case, there is no need to pull the mitral valve assembly down into the implantation site. Additional details of the transapical approach are disclosed in U.S. Patent Application Publication No. 2007/0112422 (mentioned above).

In another embodiment, the valve assembly 20 can be mounted on an expandable balloon of a delivery catheter and expanded to its functional size by inflation of the balloon. When using a balloon catheter, the valve assembly can be advanced from the introducer to initially position the valve assembly in the left atrium 26. The balloon can be inflated to fully expand the valve assembly. The delivery catheter can then be retracted to pull the expanded valve assembly into the desired implantation site (e.g., just below the annulus of the native valve). In another embodiment, the balloon initially can be partially inflated to partially expand the valve assembly in the left atrium. The delivery catheter can then be retracted to pull the partially expanded valve into the implantation site, after which the valve assembly can be fully expanded to its functional size.

Mitral regurgitation can occur over time due to the lack of coaptation of the leaflets in the prosthetic mitral valve assembly. The lack of coaptation in turn can lead to blood being regurgitated into the left atrium, causing pulmonary congestion and shortness of breath. To minimize regurgitation, the leaflets of the valve assembly can be connected to one or more tension members that function as prosthetic chordae tendinae.

Figure 9:
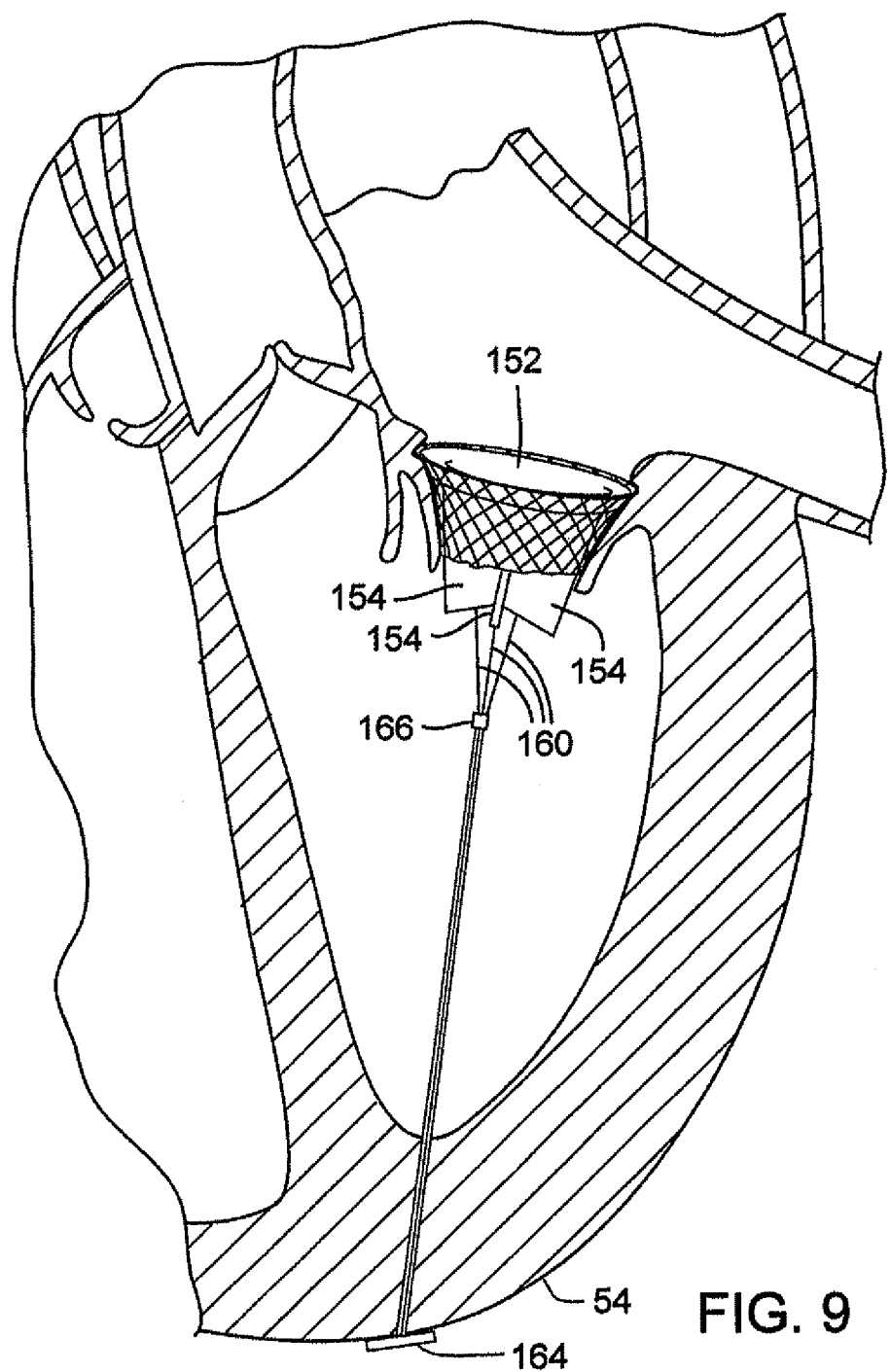
FIG. 9 is a perspective view of an embodiment of a prosthetic valve assembly having tensioning members coupled to prosthetic leaflets of the valve to simulate chordae tendinae.

FIG. 9, for example, shows an embodiment comprising a prosthetic mitral valve assembly 152 having leaflets 154. Each leaflet 154 can be connected to a respective tension member 160, the lower ends of which can be connected at a suitable location on the heart. For example, the lower end portions of tension members 160 can extend through the apex 54 and can be secured at a common location outside the heart. Tension members may be attached to or through the papillary muscles. The lower ends of tension members can be connected to an enlarged head portion, or anchor, 164, which secures the tension members to the apex. Tension members 160 can extend through a tensioning block 166. The tensioning block 166 can be configured to slide upwardly and downwardly relative to tension members 160 to adjust the tension in the tensioning members. For example, sliding the tensioning block 166 upwardly is effective to draw the upper portions of the tension members closer together, thereby increasing the tension in the tension members. The tensioning block 166 desirably is configured to be retained in place along the length of the tension members, such as by crimping the tensioning block against the tension members, once the desired tension is achieved. The tension members can be made of any suitable biocompatible material, such as traditional suture material, GORE-TEX®, or an elastomeric material, such as polyurethane. The tension members 160 further assist in securing the valve assembly in place by resisting upward movement of the valve assembly and prevent the leaflets 154 from everting so as to minimize or prevent regurgitation through the valve assembly. As such, the tethering de-stresses the moveable leaflets, particularly during ventricular systole (i.e., when the mitral valve is closed). Alternatively or in addition, the stent 10 can be connected to one or more tension members 160 for stabilizing the mitral valve assembly during the cyclic loading caused by the beating heart.

Figure 10:
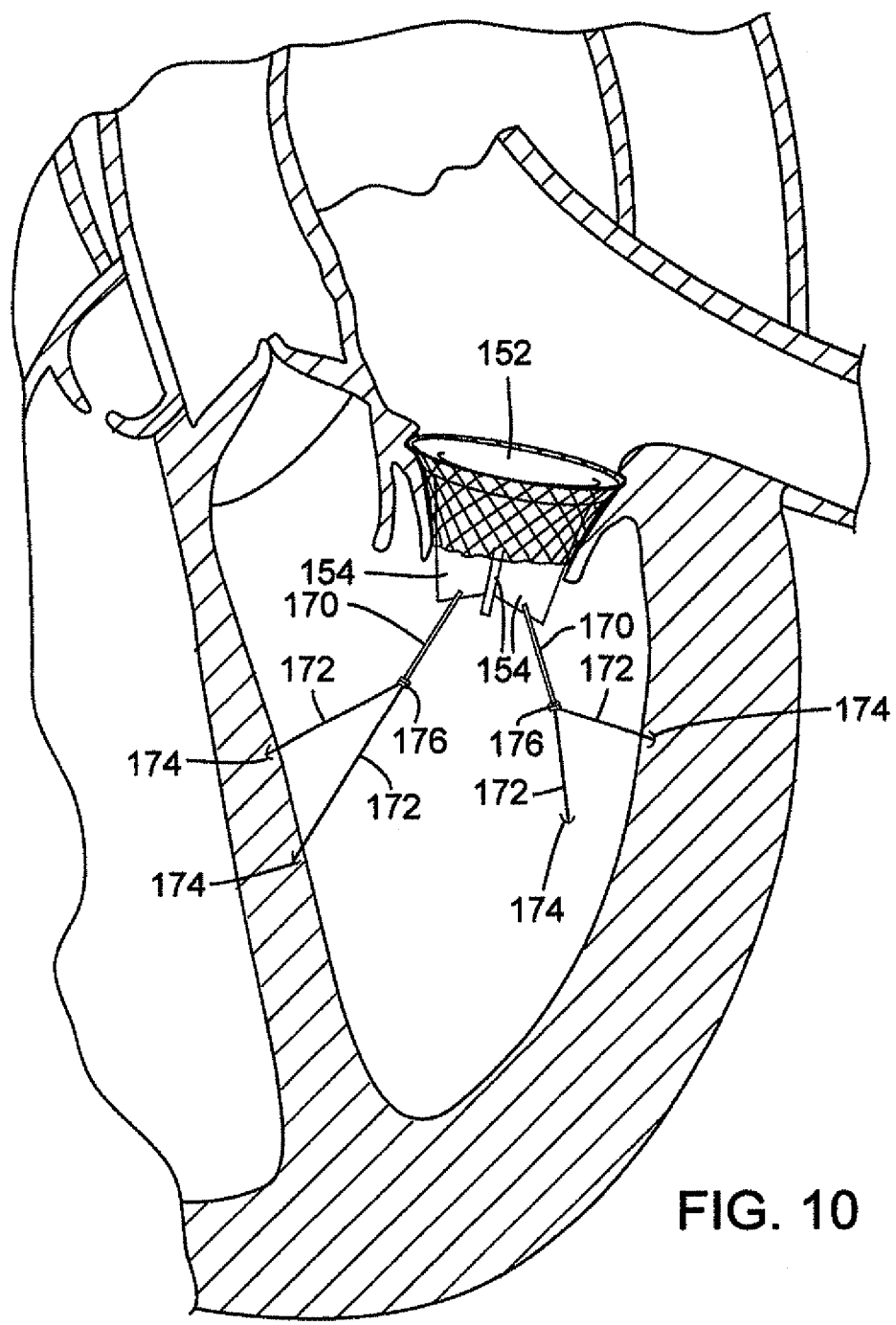
FIG. 10 is a perspective view of a prosthetic valve assembly having tensioning members, according to another embodiment.

FIG. 10 shows another embodiment of a mitral valve assembly 152 having prosthetic chordae tendinae. The prosthetic chordae tendinae comprise first and second tension members 170 connected to a respective leaflet 154 of the valve assembly. As shown, the lower end portions 172 of each tension member 170 can be connected at spaced apart locations to the inner walls of the left ventricle, using, for example, anchor members 174. A slidable tensioning block 176 can be placed over each tension member 170 for adjusting the tension in the corresponding tension member. In certain embodiments, each tension member 170 can comprise a suture line that extends through a corresponding leaflet 154 and has its opposite ends secured to the ventricle walls using anchor members 174.

In particular embodiments, the anchor member 174 can have a plurality of prongs that can grab, penetrate, and/or engage surrounding tissue to secure the device in place. The prongs of the anchor member 174 can be formed from a shape memory material to allow the anchor member to be inserted into the heart in a radially compressed state (e.g., via an introducer) and expanded when deployed inside the heart. The anchor member can be formed to have an expanded configuration that conforms to the contours of the particular surface area of the heart where the anchor member is to be deployed, such as described in co-pending application Ser. No. 11/750,272, published as US 2007/0270943 A1, which is incorporated herein by reference. Further details of the structure and use of the anchor member are also disclosed in co-pending application Ser. No. 11/695,583 to Rowe, filed Apr. 2, 2007, which is incorporated herein by reference.

Alternative attachment locations in the heart are possible, such as attachment to the papillary muscle (not shown). In addition, various attachment mechanisms can be used to attach tension members to the heart, such as a barbed or screw-type anchor member. Moreover, any desired number of tension members can be attached to each leaflet (e.g., 1, 2, 3 . . . etc.). Further, it should be understood that tension members (e.g., tension members 160 or 170) can be used on any of the embodiments disclosed herein.

As discussed above, FIGS. 9-10 show the use of tension members that can mimic the function of chordae. The tethers can have several functions including preventing the valve from migrating into the left atrium, de-stressing the leaflets by preventing eversion, and preserving ventricular function by maintaining the shape of the left ventricle. In particular, the left ventricle can lose its shape over time as the natural chordae become stretched or break. The artificial chordae can help to maintain the shape. Although FIGS. 9 and 10 show a tricuspid valve, a bicuspid valve can be used instead. Particular bicuspid valves are shown in FIGS. 12-16.

Figure 11:
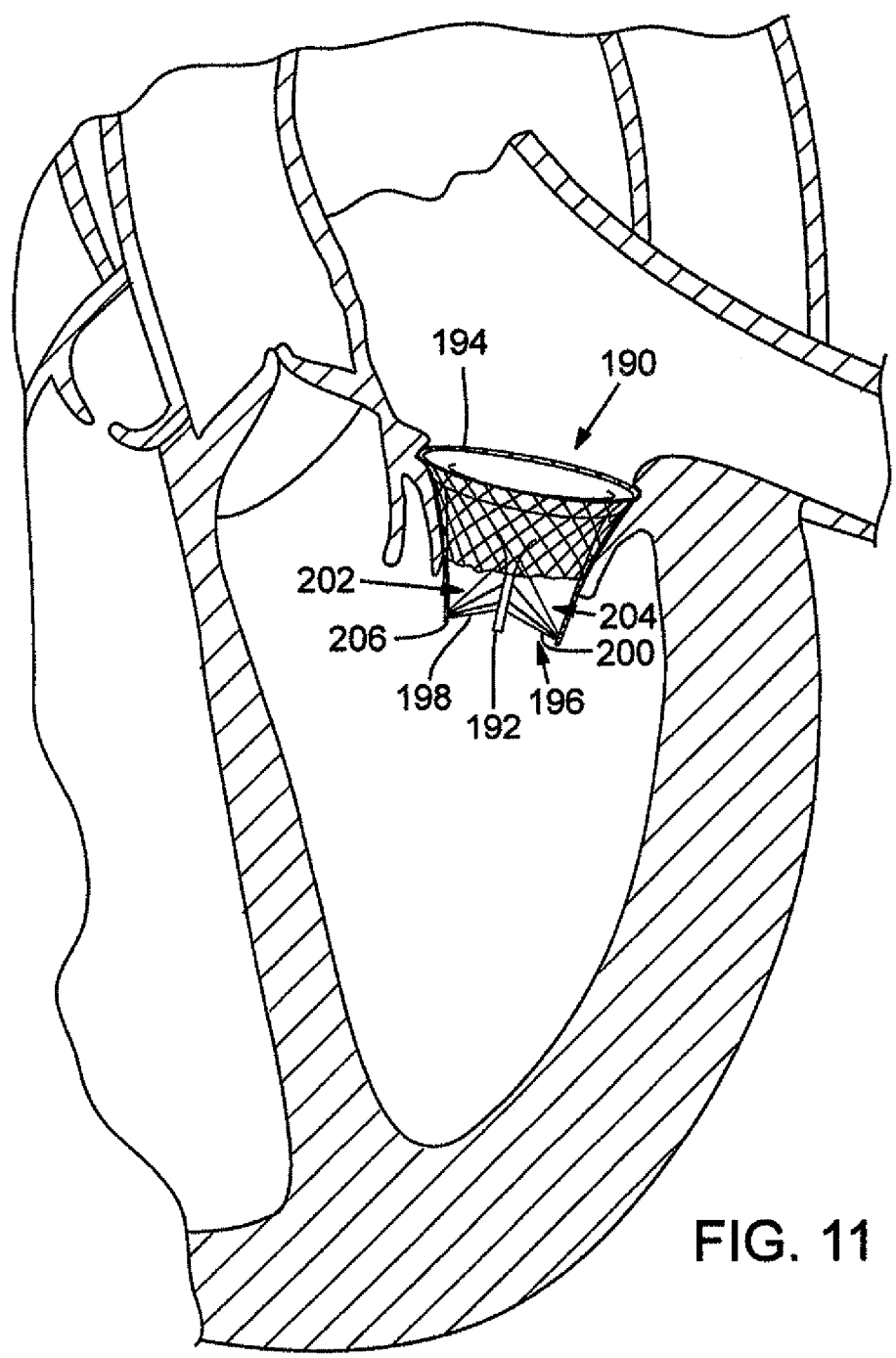
FIG. 11 is a perspective view of a prosthetic valve assembly having tensioning members, according to another embodiment.

FIG. 11 shows another embodiment of a mitral valve assembly 190 including a valve 192 and a stent 194 (shown partially cut-away to expose a portion of the valve). Tension members, shown generally at 196, can be connected between leaflets 198, 200 of the valve 192 and the stent itself. Only two leaflets are shown, but additional tension members can be used for a third leaflet in a tricuspid valve. In the illustrated embodiment, the tension members 196 can include groups 202, 204 of three tension members each. The three tension members 196 of group 202 can be attached, at one end, to leaflet 198 at spaced intervals and converge to attach at an opposite end to a bottom 206 of the stent 194. Group 204 can be similarly connected between leaflet 200 and the bottom 206 of the stent 194. The tension members 196 can be made of any suitable biocompatible material, such as traditional suture material, GORE-TEX®, or an elastomeric material, such as polyurethane. The tension members can prevent the leaflets 198, 200 from everting so as to minimize or prevent regurgitation through the valve assembly. As such, the tension members de-stress the moveable portions of the leaflets when the leaflets close during systole without the need to connect the tension members to the inner or outer wall of the heart.

Although groups of three tension members are illustrated, other connection schemes can be used. For example, each group can include any desired number of tension members (e.g., 1, 2, 3, . . . etc.). Additionally, the tension members can connect to any portion of the stent 194 and at spaced intervals, if desired. Likewise, the tension members can connect to the leaflets at a point of convergence, rather than at spaced intervals. Further, the tension members can be used on bicuspid or tricuspid valves. Still further, it should be understood that tension members extending between the stent and the leaflets can be used on any of the embodiments disclosed herein.

FIGS. 12-14 show another embodiment of a mitral valve assembly 220 including a bicuspid valve 222 mounted within a stent 224. The bicuspid valve 222 can include two unequally-sized leaflets, 226, 228. FIG. 12 shows a perspective view of the mitral valve assembly 220 with the bicuspid valve 222 in an open position with blood flow shown by directional arrow 230. FIG. 14 shows a top view of the mitral valve assembly 220 with the valve 222 in the open position. FIG. 13 shows a top view of the mitral valve assembly 220 with the bicuspid valve 222 in a closed position. The leaflet 226 is shown as a larger leaflet than leaflet 228 with the leaflets overlapping in a closed or at-rest position. The overlapping configuration can provide sufficient closure of the valve to prevent central or coaptation leakage and can enhance valve durability by eliminating or minimizing impacts on the leaflet touching or coaptation. The bicuspid valve 222 can be used with any of the stent configurations described herein.

Figure 15:
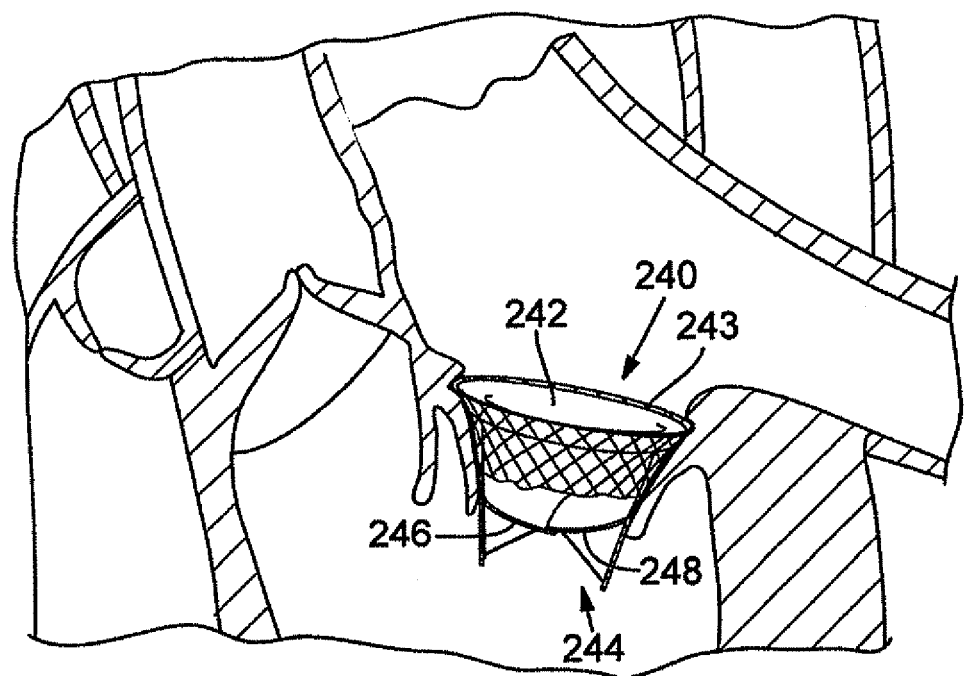
FIG. 15 is a perspective view of a prosthetic valve assembly having tensioning members coupled to a bicuspid valve in a closed position, according to another embodiment.
Figure 16:
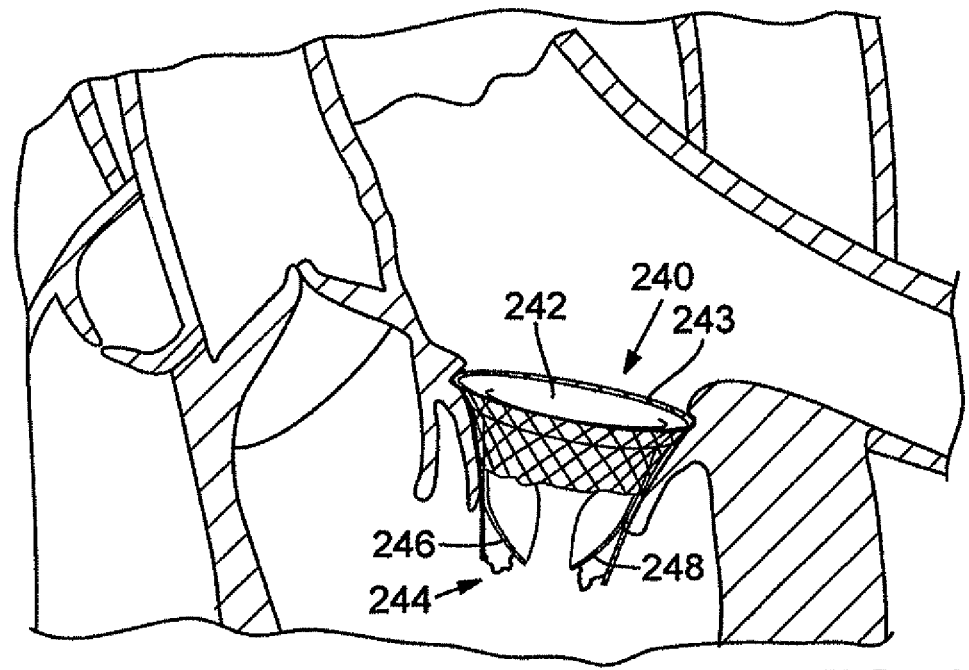
FIG. 16 is a perspective view of the prosthetic valve assembly of FIG. 15 with the bicuspid valve in an open position.

FIGS. 15 and 16 show another embodiment of a mitral valve assembly 240 including a bicuspid valve 242 mounted within a stent 243. Tension members, shown generally at 244, can be connected between leaflets 246, 248 of the valve and the stent itself. Leaflet 246 is shown as a larger leaflet that overlaps leaflet 248. FIG. 15 shows the mitral valve assembly 240 in a closed position with the tension members 244 at full extension. FIG. 16 shows the bicuspid valve 242 in the open position with the tension members 244 in a relaxed or slack state. Although the tension members 244 are shown attached at the same relative vertical position or height on the stent 243, the tension members 244 can be attached asymmetrically relative to each other. In other words, the tension members 244 can be attached at different heights along the length of the stent. Additionally, the tension members 244 can differ in length in order to achieve the asymmetrical coupling between the leaflets 246, 248 and the stent 243. The tensioning members 244 can be used on any of the mitral valve assembly embodiments described herein.

FIG. 17 shows a top view of a mitral valve assembly 260 having a non-uniform cross-sectional shape. The mitral valve assembly 260 can have a shape configured to conform to the natural opening of the native mitral valve. For example, the mitral valve assembly 260 can have a substantially "D" shape, with a substantially straight portion 262 and a substantially curved portion 264. When implanted, the substantially straight portion 262 can extend along the anterior side of the native mitral valve and the substantially curved portion 264 of the stent can extend along the posterior side of the native mitral valve. Other shapes may also be used.

Having illustrated and described the principles of the illustrated embodiments, it will be apparent to those skilled in the art that the embodiments can be modified in arrangement and detail without departing from such principles.

Although the transapical procedure shown in FIGS. 8A-8D illustrates positioning and deployment of mitral valve assembly 20, other embodiments of the mitral valve assembly disclosed herein can be implanted using the same procedure, such as the mitral valve assembly 100 of FIG. 6, or a mitral valve assembly using the stent of FIG. 7.

Further, although the mitral valve assembly 20 is shown generally circular in cross section, as noted above, it can have a D-shape, an oval shape or any other shape suitable for fitting the contours of the native mitral valve. Furthermore, although the mitral valve assembly is shown as having a flared upper end, other embodiments are contemplated, such as, for example, wherein the stent is flared at both ends or has a substantially cylindrical shape. Furthermore, the stent may be coated to reduce the likelihood of thrombi formation and/or to encourage tissue ingrowth using coatings known in the art. Still further, it is contemplated that the stent may be replaced with an alternative structure, such as an expandable tubular structure, which is suitable for anchoring the prosthetic valve member in the heart.

Still further, although a transapical procedure is described in detail in FIGS. 8A-8D, other procedures can be used in conjunction with the above-described embodiments. For example, U.S. Patent Publication 2004/0181238, to Zarbatany et al., entitled "Mitral Valve Repair System and Method for Use", which is hereby incorporated by reference, discloses a percutaneous delivery approach. A guidewire capable of traversing the circulatory system and entering the heart of the patient can be introduced into the patient through an endoluminal entry point, such as the femoral vein or the right jugular vein. The guidewire can then be directed into the right atrium where it traverses the right atrium and punctures the atrial septum using a tran-septal needle. The guidewire can then be advanced through the atrial septum, through the left atrium and through the mitral valve. Once the guidewire is properly positioned, a guide catheter can be attached to the guidewire and advanced proximate the native mitral valve. A delivery catheter for delivery of the prosthetic mitral valve can then be advanced through the guide catheter to deploy the prosthetic valve within the native mitral valve. Various delivery catheters can be used, such as those described in Zarbatany, as well as those described U.S. Patent Publication 2007/0088431, to Bourang et al., entitled "Heart Valve Delivery System With Valve Catheter" and U.S. Patent Publication U.S. 2007/0005131, to Taylor, entitled "Heart Valve Delivery System", both of which are hereby incorporated by reference.

In view of the many possible embodiments, it will be recognized that the illustrated embodiments include only examples of the invention and should not be taken as a limitation on the scope of the invention. Rather, the invention is defined by the following claims. We therefore claim as the invention all such embodiments that come within the scope of these claims.

We claim:

1. A prosthetic mitral valve assembly, comprising:
   a self-expanding stent comprising an upper portion defining an inlet end of the stent having a first diameter, a lower portion defining an extreme outlet end of the stent having a second diameter, and an intermediate portion between the upper portion and the lower portion, the intermediate portion having a third diameter, the stent tapering from the inlet end to the intermediate portion and further tapering from the intermediate portion to the extreme outlet end such that the third diameter is less than the first diameter, and the second diameter is less than the third diameter, wherein the inlet end comprises a flared end sized to be positioned above an annulus of the native mitral valve, wherein the flared end is defined by a circumferentially extending row of struts that extends continuously around the entire extent of a circumference of the upper portion, wherein the flared end is sized such that when implanted, an atrial-most end of the prosthetic mitral valve assembly contacts supra-annular tissue continuously around the entire extent of a circumference of the upper portion;
   a tether having a first end portion and a second end portion, the first end portion coupled to the lower portion of the stent, the tether being sized to extend through the left ventricle with the second end portion extending through a wall of the left ventricle at the apex of the heart; and
   a tissue anchor connected to the second end portion of the tether and configured to be implanted against an outer surface of the left ventricle at the apex such that when the prosthetic mitral valve assembly is implanted, the tether resists migration of the stent in a direction toward the left atrium and the flared end of the stent resists migration of the stent in a direction toward the left ventricle;
   wherein the prosthetic mitral valve assembly is held in place without clamping onto tissue of the annulus of the native mitral valve;
   wherein the prosthetic mitral valve assembly is adapted to be advanced in a radially compressed state along a distal end of the delivery catheter for insertion through the wall of the heart.

2. The prosthetic mitral valve assembly of claim 1, wherein the stent has a truncated conical shape.

3. The prosthetic mitral valve assembly of claim 1, wherein the stent is made of nitinol.

4. The prosthetic mitral valve assembly of claim 1, wherein the tether comprises a bioresorbable material.

5. The prosthetic mitral valve assembly of claim 1, wherein the stent has a substantially D-shape cross-section for conforming to the native mitral valve.

6. The prosthetic mitral valve assembly of claim 1, further comprising a valve portion having three prosthetic leaflets formed of porcine pericardium and mounted within an interior portion of the stent, the valve portion having leaflets for occluding blood flow in one direction and replacing the function of the native mitral valve.

7. The prosthetic mitral valve assembly of claim 6, wherein the valve portion is mounted within the lower portion of the stent.

8. The prosthetic mitral valve assembly of claim 1, wherein the tissue anchor comprises an enlarged head portion.

9. The prosthetic mitral valve assembly of claim 1, wherein the stent has a length between 15 and 50 mm.

10. The prosthetic mitral valve assembly of claim 1, wherein the stent has a continuous taper.

* * * * *